US011980489B2

(12) United States Patent
Suzuki

(10) Patent No.: US 11,980,489 B2
(45) Date of Patent: May 14, 2024

(54) RADIATION IMAGING APPARATUS

(71) Applicant: CANON KABUSHIKI KAISHA, Tokyo (JP)

(72) Inventor: Masataka Suzuki, Kanagawa (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 17/592,718

(22) Filed: Feb. 4, 2022

(65) Prior Publication Data
US 2022/0249041 A1 Aug. 11, 2022

(30) Foreign Application Priority Data

Feb. 8, 2021 (JP) ................................. 2021-018275

(51) Int. Cl.
G01T 1/20 (2006.01)
A61B 6/00 (2006.01)
A61B 6/42 (2024.01)

(52) U.S. Cl.
CPC .............. A61B 6/4283 (2013.01); A61B 6/44 (2013.01); G01T 1/20 (2013.01)

(58) Field of Classification Search
CPC ....... A61B 6/4283; A61B 6/44; A61B 6/4233; G01T 1/20; G01T 1/244; G01N 23/04; H05K 5/03
See application file for complete search history.

(56) References Cited

U.S. PATENT DOCUMENTS

| | | | | |
|---|---|---|---|---|
| 6,825,472 B2 * | 11/2004 | Endo | ....................... | G01T 1/244 250/336.1 |
| 6,897,449 B1 * | 5/2005 | Hata | ..................... | G01T 1/2928 250/370.11 |
| 7,514,703 B2 * | 4/2009 | Iwakiri | ................... | G03B 42/02 250/584 |
| 7,569,831 B2 * | 8/2009 | Jadrich | .................. | G03B 42/04 250/370.11 |
| 7,582,877 B2 * | 9/2009 | Dobrusskin | ............ | G03B 42/04 250/370.09 |
| 7,638,773 B2 * | 12/2009 | Kuwabara | .............. | G03B 42/04 250/370.08 |
| 7,663,114 B2 * | 2/2010 | Aoyagi | ................. | G01T 1/2928 250/370.09 |
| 7,777,192 B2 * | 8/2010 | Ohta | ...................... | A61B 6/563 250/370.09 |

(Continued)

FOREIGN PATENT DOCUMENTS

WO 2017/145444 A1 8/2017

Primary Examiner — David P Porta
Assistant Examiner — Djura Malevic
(74) Attorney, Agent, or Firm — VENABLE LLP

(57) ABSTRACT

A mechanism that enhances rigidity of a casing of a radiation imaging apparatus while effectively using limited space inside the casing is provided. The rectangular casing that contains a radiation detecting panel, the radiation detecting panel detecting incident radiation, includes a front cover including an incident surface on which the radiation is incident, and a rear cover disposed in a manner to be opposite to the front cover. The rear cover includes one or more recess portions and a rib, at least one end of the rib being connected to a recess portion of the one or more recess portions, at a bottom surface opposite to the incident surface.

13 Claims, 7 Drawing Sheets

(56) References Cited

U.S. PATENT DOCUMENTS

| | | | | |
|---|---|---|---|---|
| 7,947,960 B2* | 5/2011 | Wu | | G03B 42/02 |
| | | | | 250/370.09 |
| 8,744,044 B2* | 6/2014 | Suwa | | G03B 42/04 |
| | | | | 378/62 |
| 8,804,171 B2* | 8/2014 | Suzuki | | G03G 15/55 |
| | | | | 358/1.14 |
| 9,104,097 B2* | 8/2015 | Suwa | | A61B 6/4283 |
| 9,535,165 B2* | 1/2017 | Takatori | | G01T 1/17 |
| 9,978,234 B2* | 5/2018 | Kano | | G08B 13/19 |
| 10,024,980 B2* | 7/2018 | Suzuki | | G03B 42/04 |
| 10,061,042 B2 | 8/2018 | Suzuki et al. | | |
| 10,119,859 B2* | 11/2018 | Suzuki | | G01T 1/2018 |
| 10,122,847 B2* | 11/2018 | Alameh | | H04M 3/02 |
| 10,185,039 B2* | 1/2019 | Ergler | | G01T 1/243 |
| 10,192,646 B2* | 1/2019 | Lee | | H01L 27/14676 |
| 10,274,613 B2* | 4/2019 | Suzuki | | A61B 6/4283 |
| 10,459,094 B2* | 10/2019 | Simanovsky | | G01T 1/2018 |
| 10,488,532 B2* | 11/2019 | Abenaim | | G01T 1/2018 |
| 10,648,854 B2* | 5/2020 | Suzuki | | G01J 1/4228 |
| 10,722,195 B2* | 7/2020 | Suwa | | A61B 6/4283 |
| 10,914,845 B2* | 2/2021 | Sakuragi | | H02J 50/10 |
| 11,141,120 B2* | 10/2021 | Sakuragi | | A61B 6/102 |
| 2003/0174464 A1* | 9/2003 | Funawatari | | G11B 25/043 |
| 2004/0227096 A1* | 11/2004 | Yagi | | G01T 1/2928 |
| | | | | 378/189 |
| 2005/0017188 A1* | 1/2005 | Yagi | | G01T 1/244 |
| | | | | 250/370.09 |
| 2005/0056789 A1* | 3/2005 | Spahn | | A61B 6/4233 |
| | | | | 348/E5.027 |
| 2007/0138400 A1* | 6/2007 | Ertel | | G01T 1/1644 |
| | | | | 250/370.11 |
| 2007/0272873 A1* | 11/2007 | Jadrich | | G01T 1/20 |
| | | | | 250/370.11 |
| 2008/0078940 A1* | 4/2008 | Castleberry | | G01T 1/20189 |
| | | | | 250/370.09 |
| 2009/0202038 A1* | 8/2009 | Wu | | A61B 6/4429 |
| | | | | 378/198 |
| 2011/0255127 A1* | 10/2011 | Suzuki | | G03G 15/55 |
| | | | | 358/1.15 |
| 2015/0293237 A1* | 10/2015 | Suzuki | | G01T 1/2018 |
| | | | | 250/369 |
| 2017/0038252 A1* | 2/2017 | Suzuki | | A61B 6/102 |
| 2017/0090044 A1* | 3/2017 | Suzuki | | G01T 1/2018 |
| 2017/0372572 A1* | 12/2017 | Kano | | C22C 23/00 |
| 2018/0321392 A1* | 11/2018 | Suzuki | | G03B 42/04 |
| 2019/0025116 A1* | 1/2019 | Suzuki | | G03B 42/04 |
| 2019/0310383 A1* | 10/2019 | Sakuragi | | A61B 6/4216 |
| 2020/0100739 A1 | 4/2020 | Horiuchi et al. | | |

* cited by examiner

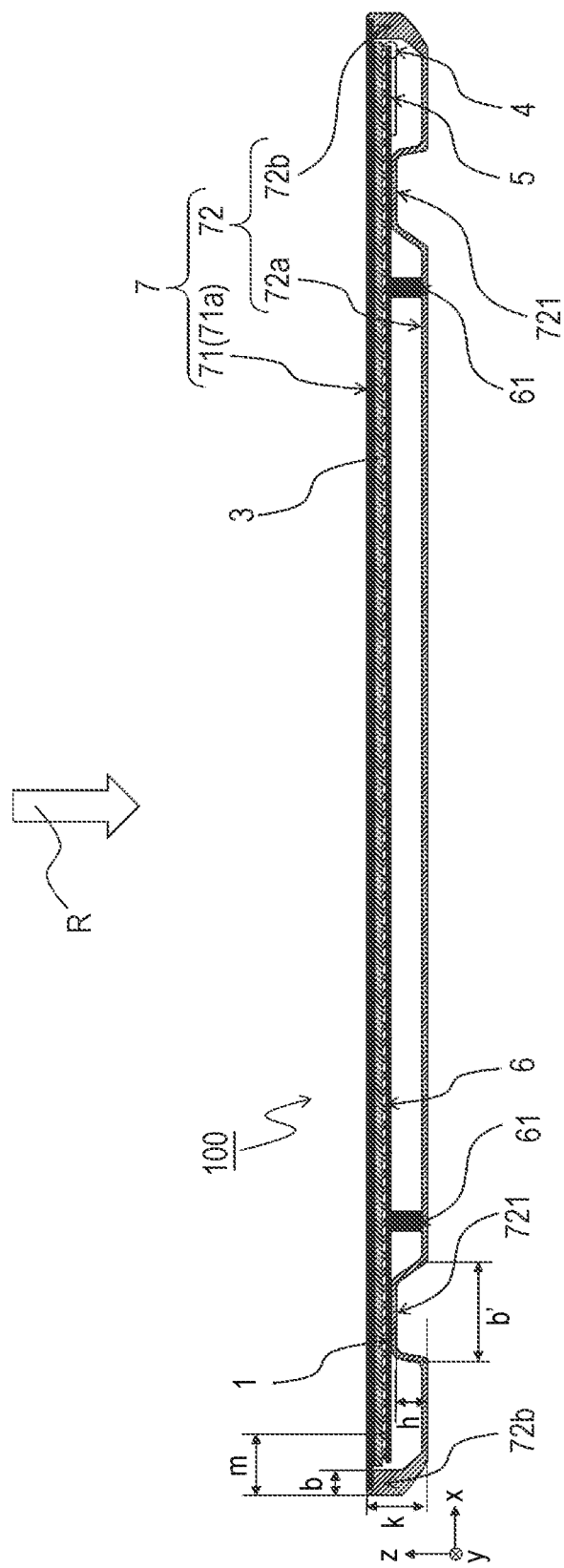

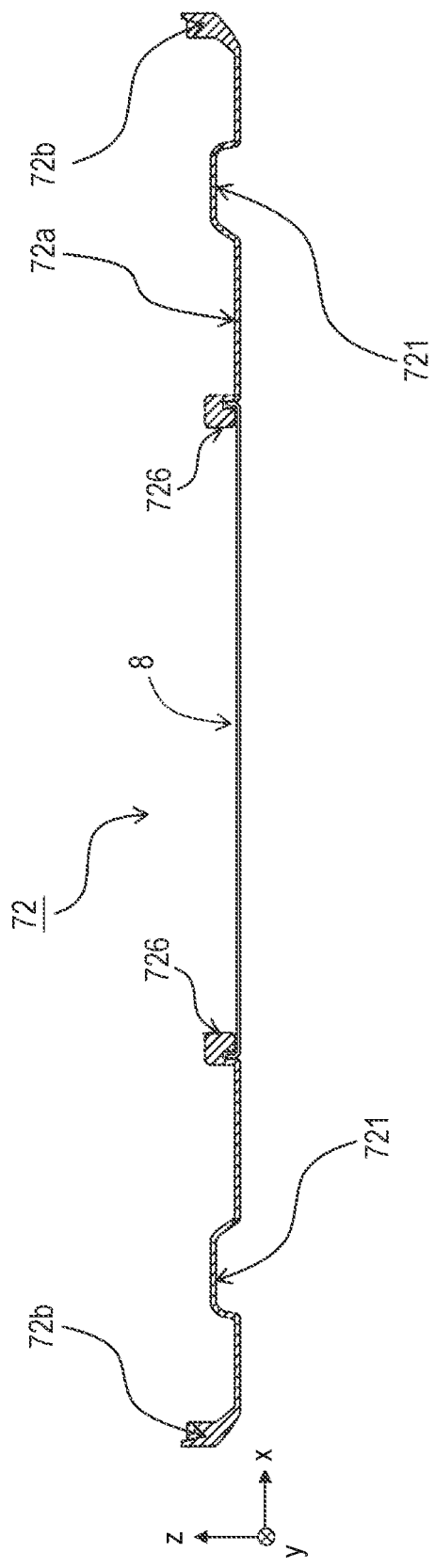

RADIATION IMAGING APPARATUS

BACKGROUND OF THE INVENTION

Field of the Invention

The present invention relates to a radiation imaging apparatus that takes a radiation image.

Description of the Related Art

Radiation imaging apparatuses that acquire a radiation image by detecting an intensity distribution of radiation that has penetrated through a subject (hereinafter, "imaging apparatus(s)") have widely been used in industrial non-destructive testing or medical diagnosis. When an image is taken, it is conceivable that an external force is applied to the apparatus because the apparatus is directly put on, e.g., a patient, which is a subject. In addition, in the case of a portable imaging apparatus, it is conceivable that an impactive force is applied to the apparatus if the apparatus is dropped when handled. For maintenance of user-friendliness and proper protection of internal components, the imaging apparatuses each need to be designed in consideration of deformation, distortion and the like occurring when an external force is provided to the apparatus. Moreover, the imaging apparatuses each need to be enhanced in portability and reduced in weight.

International Publication No. WO2017/145444 discloses a portable radiation image imaging apparatus that is provided with a recess in a casing for enhancement in strength of the casing and enhancement in portability and that includes two components forming the casing, the two components being movable relative to each other in a certain direction so that distortion occurred upon application of a force to the casing is less likely to remain. In addition, U.S. Patent Application Publication No. 2020/0100739 discloses a radiation detecting apparatus with rigidity of a casing enhanced by devising a configuration of ribs at the casing in order to properly shockproof a radiation detecting panel.

However, as described in International Publication No. WO2017/145444, two components forming a casing being removable relative to each other in a certain direction means that connection of the two components forming the casing is not complete in the certain direction. Therefore, there is the problem of rigidity of the casing being easily lowered. Further, it may be difficult to ensure sealability for, e.g., waterproof.

On the other hand, as described in U.S. Patent Application Publication No. 2020/0100739, where rigidity of a casing is enhanced by providing ribs to the casing, it is necessary to properly dispose the ribs in such a manner that a weight increase is curbed. In addition, since the ribs take up internal space of the imaging apparatus, it is necessary to enhance the rigidity of the casing with a smallest possible number of ribs disposed.

An aspect of the present invention has been made in view of the aforementioned problems, and aims to provide a radiation imaging apparatus with rigidity of a casing of the imaging apparatus enhanced while limited space inside the casing being efficiently used.

SUMMARY OF THE INVENTION

A radiation imaging apparatus according to an aspect of the present invention includes: a radiation detecting panel arranged to detect incident radiation; and a rectangular casing arranged to contain the radiation detecting panel. The casing includes a front cover including an incident surface on which the radiation is incident, and a rear cover disposed in a manner to be opposite to the front cover. The rear cover includes one or more recess portions and a recess portion-connected rib, at least one end of the recess portion-connected rib being connected to a recess portion of the one or more recess portions, at a bottom surface opposite to the incident surface.

Further features of the present invention will become apparent from the following description of exemplary embodiments with reference to the attached drawings.

BRIEF DESCRIPTION OF THE DRAWINGS

FIG. 2 is a sectional diagram illustrating an example of an internal configuration in a section along A-A indicated in FIG. 1B.

FIG. 5 is a sectional diagram illustrating an example of an internal configuration in a section along B-B indicated in FIG. 4B.

DESCRIPTION OF THE EMBODIMENTS

Exemplary embodiments for implementing the present invention will now be described in detail in accordance with the accompanying drawings. Note that details of dimensions and structures indicated in the below-described embodiments of the present invention are not limited to those described in the specification or drawings. In addition, for radiation according to the present invention, for example, X-rays can be used; however, examples of radiation used in the present invention include, e.g., $\alpha$ rays, $\beta$ rays, $\gamma$ rays, corpuscular rays, cosmic rays, and the like.

First Embodiment

Figure 1A:
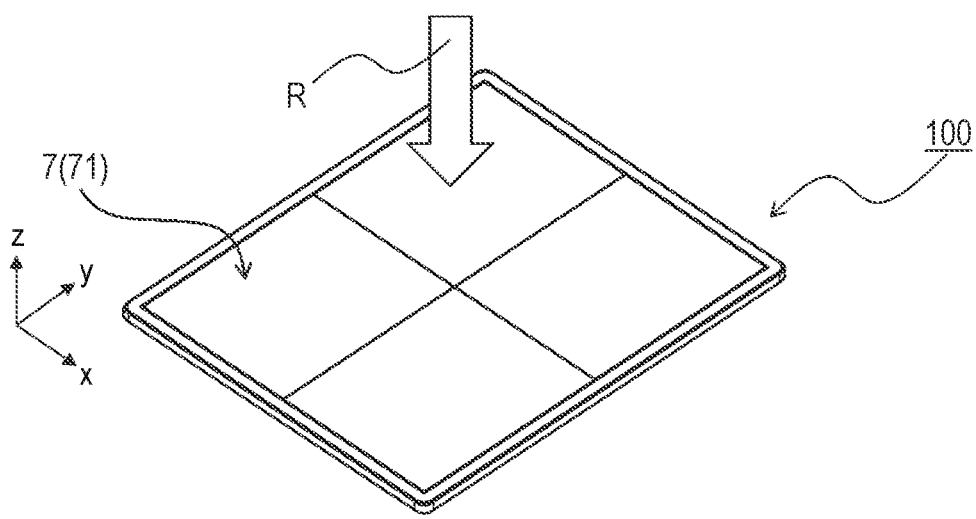
FIG. 1A is a perspective diagram illustrating an example of an outer appearance of an imaging apparatus according to a first embodiment.
Figure 1B:
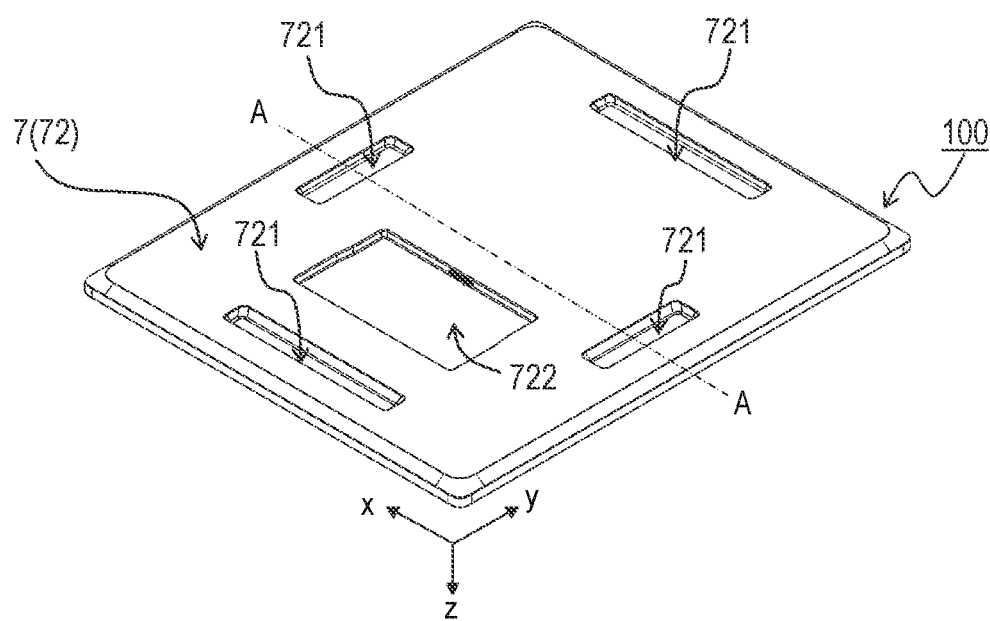
FIG. 1B is a perspective diagram illustrating an example of an outer appearance of the imaging apparatus according to the first embodiment.

FIG. 1A and FIG. 1B are diagrams each illustrating an example of an outer appearance of an imaging apparatus 100 according to a first embodiment. The imaging apparatus 100 includes a rectangular casing 7.

FIG. 1A is a perspective diagram illustrating an example of an outer appearance of the imaging apparatus 100 as viewed from a front cover 71 of the casing 7, the front cover 71 being located on the side on which radiation R (for example, radiation R that has penetrated through a subject) is incident. An x-y-z coordinate system in which a z-direction is a direction from the imaging apparatus 100 toward a radiation generating apparatus (not illustrated) that generates the radiation R and an x-direction and a y-direction are directions that are orthogonal to the z-direction and orthogonal to each other is indicated.

FIG. 1B is a perspective diagram illustrating an example of an outer appearance of the imaging apparatus 100 as viewed from a rear cover 72 of the casing 7, the rear cover 72 being disposed in such a manner as to be opposite to the front cover 71 illustrated in FIG. 1A (being located on the opposite side of the casing 7 from the side on which the radiation R is incident). In FIG. 1B, an x-y-z coordinate system corresponding to the x-y-z coordinate system indicated in FIG. 1A is indicated. In addition, in the rear cover 72, holding recess portions 721 for a user of the imaging apparatus 100 to place his/her fingers when holding the casing 7, and a battery receiving recess portion 722 for receiving a battery are formed as a plurality of recess portions. As illustrated in FIG. 1A and FIG. 1B, the holding recess portions 721 are provided near respective edges of an outer shape of the rear cover 72, respectively, as viewed from the front cover 71 side (z-direction) including an incident surface on which the radiation R is incident.

FIG. 2 is a diagram illustrating an example of an internal configuration of the imaging apparatus 100 according to the present embodiment in a section along A-A indicated in FIG. 1B. In FIG. 2, components that are similar to components illustrated in FIG. 1A and FIG. 1B are provided with reference numerals that are the same as those in FIG. 1A and FIG. 1B, and detailed description thereof is omitted. Further, in FIG. 2, an x-y-z coordinate system corresponding to the x-y-z coordinate system indicated in FIG. 1A and FIG. 1B is indicated.

The imaging apparatus 100 contains a radiation detecting panel (hereinafter, "detecting panel") 1, a buffering member 3, a flexible circuit board 4, a control board 5, a support base 6 and a casing 7.

The detecting panel 1 is a component unit that detects the radiation R emitted from, for example, a radiation generating apparatus (not illustrated) and entered through a subject, as an electrical signal for a radiation image. The detecting panel 1 is connected to the flexible circuit board 4. The electrical signal for the radiation image, the electrical signal obtained by the detecting panel 1, is transferred to, for example, an external apparatus outside the imaging apparatus 100 via the flexible circuit board 4, the control board 5, etc., and subsequently, is displayed on a display unit such as a monitor as the radiation image and used for, e.g., diagnosis.

The detecting panel 1 is, for example, what is called an indirect conversion-type detecting panel including, e.g., a sensor board with a multitude of photoelectric conversion elements (sensors) disposed in an upper portion on the side on which the radiation R is incident, a phosphor layer (scintillator layer) disposed on the upper side (side on which the radiation R is incident) of the sensor board, and a phosphor protection film. In this case, the phosphor protection film includes a material having low moisture permeability and is used for protection of a phosphor. Note that although an example in which an indirect conversion-type detecting panel is employed for the detecting panel 1 is described here, the present embodiment is not limited to this configuration. For example, a configuration in which what is called a direct conversion-type detecting panel including a sensor board that includes a radiation conversion unit with conversion elements each including, e.g., a-Se and switch elements such as TFTs arranged two-dimensionally is employed for the detecting panel 1 also falls within in the present embodiment. Note that for a material of the sensor board of the detecting panel 1, e.g., glass can be used, but, e.g., a highly flexible resin may be used, and also, the material of the sensor board is not limited to these materials.

The buffering member 3 is disposed between a front cover 71 including an incident surface 71a on which the radiation R is incident, and the detecting panel 1, and is a component unit for protecting the detecting panel 1 from, e.g., an external force applied to the casing 7. The buffering member 3 may include, for example, a foam resin or a gel.

The flexible circuit board 4 is connected to the detecting panel 1 and the control board 5.

The control board 5 is a component unit that reads an electrical signal for a radiation image from the detecting panel 1 via the flexible circuit board 4 and performs, e.g., processing of the read electrical signal for the radiation image.

The support base 6 is a component unit that supports the detecting panel 1. Bosses 61 that project to the rear cover 72 side are provided at the support base 6. The support base 6 can include, for example, any of an aluminum alloy, a magnesium alloy, a fiber reinforced resin and a resin, which are lightweight; however, in the present embodiment, a material of the support base 6 is not limited to these materials.

The casing 7 is a rectangular casing (outer covering) that contains the detecting panel 1, the buffering member 3, the flexible circuit board 4, the control board 5 and the support base 6. The casing 7 includes the front cover 71 including the incident surface 71a on which the radiation R is incident, and the rear cover 72 including a bottom surface 72a opposite to the incident surface 71a (located on the opposite side of the casing 7 from the incident surface 71a) and side surfaces 72b connecting the incident surface 71a and the bottom surface 72a. Here, side surfaces 72b of the rear cover 72 correspond to a frame portion to be joined to the front cover 71 at an outer periphery of the rear cover 72. Then, in the example illustrated in FIG. 2, holding recess portions 721 are formed in the bottom surface 72a included in the rear cover 72. Here, if the recess portions such as the holding recess portions 721 are more deeply recessed toward the detecting panel 1, the user can perform stable handling and rigidity of the casing 7 is enhanced, but space (volume) inside the casing 7 is reduced.

The rear cover 72 can include, for example, any of an aluminum alloy, a magnesium alloy, a fiber reinforced resin and a resin, which are lightweight; however, in the present embodiment, a material of the rear cover 72 is not limited to these materials. In addition, the front cover 71 can include, for example, a carbon fiber reinforced resin, which is high in transmittance of radiation R and lightweight; however, in the present embodiment, a material of the front cover 71 is not limited to these materials. The two components, the front cover 71 and the rear cover 72, included in the casing 7 are joined via, e.g., screws, a gluing agent or an adhesive agent. Here, if the front cover 71 and the rear cover 72 are joined via screws, the casing 7 can easily be disassembled. Further, if the front cover 71 and the rear cover 72 are joined via a gluing agent or an adhesive agent, it is desirable that one that allows easy disassembling after the joining is selected. Furthermore, it is desirable that the casing 7 have a waterproof property, waterproof packing may be disposed at a surface of joining between the front cover 71 and the rear cover 72. Note that although in the present embodiment, the casing 7 is configured using two components that are the front cover 71 and the rear cover 72, in the present invention, a dividing position and the number of components in the casing 7 are not limited to those in the present embodiment. For example, the rear cover 72 may include two components by dividing the bottom surface 72a and the side surfaces 72b from each other. In addition, divided surfaces may be provided in the side surfaces 72a and the front cover 71 may have a shape resulting from standing walls being provided at an outer shape like the rear cover 72, rather than a shape of a simple plate.

Furthermore, in the present embodiment, the imaging apparatus 100 includes a battery (not illustrated) that supplies necessary electric power to the detecting panel 1, the flexible circuit board 4, the control board 5, etc. The battery is configured in such a manner that the user can attach and detach the battery from and to the imaging apparatus 100, and as illustrated in FIG. 1B, the battery receiving recess portion 722 for receiving the battery is provided in the bottom surface 72a included in the rear cover 72. Here, for the battery, as an example, a lithium-ion battery, an electric double-layer capacitor or an all-solid-state battery is used; however, in the present embodiment, the battery is not limited to these examples.

Moreover, in the present embodiment, the imaging apparatus 100 may further include, e.g., an LED indicating a state of the apparatus, a switch for a user to control the imaging apparatus 100 and a connector to which a wired connection cable for communication with an external apparatus is detachably attached. Furthermore, in the present embodiment, the imaging apparatus 100 may include, e.g., an antenna for wireless communication inside the casing 7.

Figure 3A:
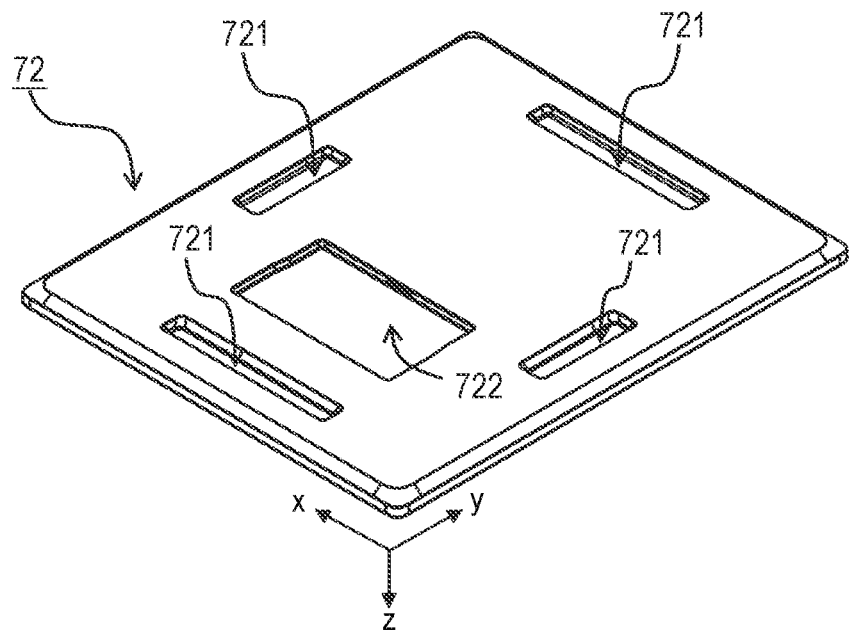
FIG. 3A is a perspective diagram illustrating an example of a schematic configuration of a rear cover in the imaging apparatus according to the first embodiment.
Figure 3B:
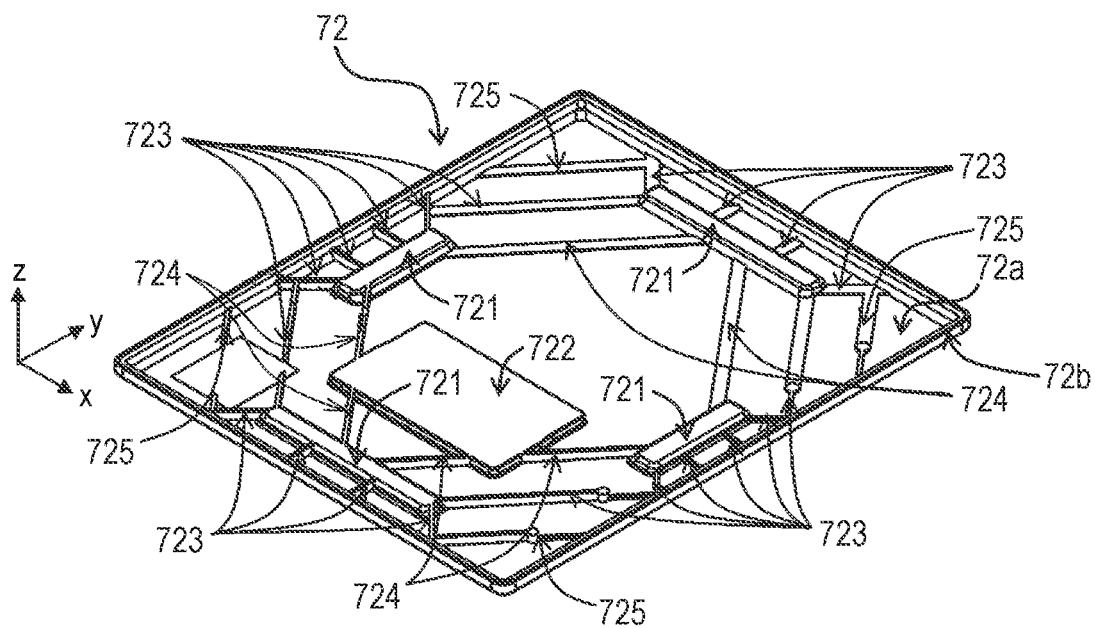
FIG. 3B is a perspective diagram illustrating an example of a schematic configuration of the rear cover in the imaging apparatus according to the first embodiment.

FIG. 3A and FIG. 3B are diagrams each illustrating an example of a schematic configuration of the rear cover 72 in the imaging apparatus 100 according to the present embodiment. In FIG. 3A and FIG. 3B, components that are similar to components illustrated in FIG. 1A to FIG. 2 are provided with reference numerals that are the same as those in FIG. 1A to FIG. 2, and detailed description thereof is omitted. In addition, in FIG. 3A and FIG. 3B, an x-y-z coordinate system corresponding to the x-y-z coordinate system indicated in FIG. 1A to FIG. 2 is indicated.

More specifically, FIG. 3A is a perspective diagram illustrating an example of an outer appearance of the rear cover 72 as viewed in a direction that is the same as that of FIG. 1B. FIG. 3B is a perspective diagram illustrating an example of an outer appearance of the rear cover 72 as viewed from the side opposite to that of FIG. 3A (front cover 71 side in the casing 7).

As illustrated in FIG. 3B, the holding recess portions 721 and the battery receiving recess portion 722, and ribs 723 to 725 for reinforcement, etc., of the rear cover 72 are provided at the bottom surface 72a of the rear cover 72. More specifically, each of the ribs 723 to 725 is a thin column-shaped reinforcing member that is, e.g., bonded to the rear cover 72. Here, in the present embodiment, each of the ribs 723 and 724 corresponds to a "recess portion-connected rib", at least one end of which is connected to a holding recess portion 721 or the battery receiving recess portion 722. Additionally, in the present embodiment, each of the ribs 725 corresponds to a "frame portion-to-frame portion connecting rib" connected to mutually adjacent edges of the frame portion including the side surfaces 72b of the casing 7 as viewed from the front cover 71 side including the incident surface 71a.

A reason that the ribs 723 to 725 are provided at the rear cover 72 in the present embodiment will be described below.

In the imaging apparatus 100, during radiation imaging, an external force is expected to be applied to the casing 7. During radiation imaging, a load may be imposed on the imaging apparatus 100 as a result of, for example, a patient stepping on the imaging apparatus 100. Further, when handling the imaging apparatus 100, the user may mistakenly drop the imaging apparatus 100. Upon such external force being applied to the imaging apparatus 100, the casing 7 of the imaging apparatus 100 deforms, causing distortion. Furthermore, a temperature change in an environment during use, transportation or storage of the imaging apparatus 100 may cause a change in volume of a structural object such as the casing 7, resulting in deformation or distortion of the casing 7 of the imaging apparatus 100. It is conceivable that the casing 7 of the imaging apparatus 100 restores to an original state from such deformation or distortion, by elimination of the external force or restoration of the temperature. However, there may also be cases where the casing 7 remains distorted because of plastic deformation and where a joining part of the casing 7 such as the part of joining between the front cover 71 and the rear cover 72 remains distorted and does not return. Such deformation or distortion of the imaging apparatus 100 may impair the user's ease of handling. In addition, the problem of a failure to properly protect components inside the imaging apparatus 100 may occur.

In order to solve these problems, in the present embodiment, the ribs 723 to 725 for curbing deformation are formed at the rear cover 72. Here, disposition of the ribs causes concerns, e.g., that the weight of the casing 7 increases and that the internal space of the casing 7 for disposition of an electric board, etc., is reduced. In view of these concerns, in the present embodiment, disposition of the ribs 723 to 725 that enables reduction in weight of the casing 7 and that minimizes reduction in internal space (volume) of the casing 7 is provided.

As described above, the holding recess portions 721 and the battery receiving recess portion 722 are formed in the bottom surface 72a of the rear cover 72. The battery (not illustrated) included in the imaging apparatus 100 according to the present embodiment needs to have a certain amount of volume in order to supply necessary electric power to the respective component units inside the casing 7, and thus, a space corresponding to the volume is needed for the battery receiving recess portion 722. Here, a depth of the battery receiving recess portion 722 is desirably no less than 3.0 mm in consideration of a thickness of the battery. In addition, a maximum depth of each of the holding recess portions 721 that the user uses during handling is desirably a depth that is deeper than a gravity center of the casing 7 or a depth that is no less than half a thickness of the casing 7 (h in FIG. 2) in a thickness direction of the casing 7 (z-direction in FIG. 2, which is a direction in which radiation R is incident). This is because when the user holds the holding recess portions 721, the user's force for the holding can be reduced. Even in a case where no such deep depth can be provided, in order to stabilize holding of the imaging apparatus 100, the maximum depth of each of the holding recess portions 721 is desirably no less than 5 mm.

Although in the present embodiment, maximum depths of two types of recess portions, the holding recess portions 721 and the battery receiving recess portion 722, are the same and are both 8.0 mm, in the present invention, the maximum depths are not limited to this example and the maximum depths of the respective recess portions may be different from each other. Here, the holding recess portions 721 and the battery receiving recess portion 722, and the frame portion including the side surfaces 72b of the casing 7 each have a shape that is tall in a thickness direction of the imaging apparatus 100 in comparison with a thickness of a plate including the bottom surface 72a of the casing 7, and thus, contribute to enhancement in rigidity of the rear cover 72.

As illustrated in FIG. 3B, each of the ribs 723 is a rib connected to the frame portion including the side surfaces 72b of the casing 7 and to a holding recess portion 721. Further, each of the ribs 724 is a rib connected to recess portions (to holding recess portions 721 or to a holding recess portion 721 and to the battery receiving recess portion 722). Furthermore, each of the ribs 725 is a rib connected to edges (more specifically, edges adjacent to each other) of the frame portion including the side surfaces 72b of the casing 7. This disposition of the ribs 723 to 725 is intended to effectively enhance the rigidity of the entire rear cover 72 relative to the weight of the casing 7 by connecting the frame portion and the recess portions (including the holding recess portions 721 and the battery receiving recess portion 722), which each have high rigidity, via the ribs.

In the present embodiment, respective maximum heights of the ribs 723 to 725 are determined in such a manner that respective positions of maximum height parts of the ribs, and positions of respective maximum depth parts of the holding recess portions 721 and the battery receiving recess portion 722 in an internal surface of the casing 7 coincide with each other in the thickness direction of the casing 7. In addition, the maximum height parts of the ribs are in contact with the support base 6. In reality, a resin sheet material (not illustrated) or the like may be interposed in such a manner that the support base 6 and the rear cover 72 are electrically insulated from each other.

Note that in the present embodiment, some of the ribs are adjusted in height in order to prevent interference with, e.g., the electric board (not illustrated) or a cable (not illustrated) disposed inside the casing 7. Furthermore, there are also ribs each including a cut in a part thereof to allow easy disposition of the cable, etc. In addition, even where it is difficult to connect the respective recess portions (including the holding recess portions 721 and the battery receiving recess portion 722) and/or parts of the frame portion via ribs, even merely connecting the recess portions (including the holding recess portions 721 and the battery receiving recess portion 722), which have high rigidity, and ribs is effective for enhancement in flexural rigidity of the entire rear cover 72 relative to the weight of the casing 7.

Next, orientations of the ribs 723 to 725 will be described. As illustrated in FIG. 3B, the frame portion of the casing 7 is provided at the side surfaces 72b of the rear cover 72 in such a manner as to extend along the outer shape (outer periphery) of the rear cover 72. In the present embodiment, the frame portion including the side surfaces 72b of the casing 7 continuously extend around the outer periphery of the rear cover 72, but may include a cut or a discontinuous surface in a part thereof. Here, the frame portion including the side surfaces 72b of the casing 7 is tall in the thickness direction of the imaging apparatus 100 (z-direction) as indicated by the length of "k" in FIG. 2. Therefore, the frame portion contributes to enhancement in flexural rigidity in directions that are parallel to the x-direction or the y-direction. However, flexural rigidity in, e.g., directions of diagonals of an x-y plane of the rear cover 72 is relatively low. In addition, the bottom surface 72a easily deforms in a torsional direction (direction in which the rear cover 72 is twisted with respect to an axis on the x-y plane such as an x-axis or a y-axis) if the bottom surface 72a has a simple plate-like shape. Therefore, depending on the direction of an external force applied to the imaging apparatus 100 or conditions for supporting the imaging apparatus 100 when an external force is applied to the imaging apparatus 100, the casing 7 of the imaging apparatus 100 may easily deform and be distorted.

In order to respond to such problem, the present inventor studied maximization of flexural rigidity (minimization of mechanical compliance) in the directions of the diagonals of the rear cover 72 relative to the weight of the casing 7. As a result, the present inventor found that connecting the ribs 723 to 725 to the high-rigidity recess portions (including the holding recess portions 721 and the battery receiving recess portion 722) and/or the frame portion is effective. At the same time, with regard to orientations of the ribs 723 to 725, the present inventor conceived of forming the ribs 723 to 725 in directions that are substantially parallel to the directions of the diagonals of the rear cover 72 of the casing 7 in the x-y plane as viewed from the front cover 71 side including the incident surface 71a. Consequently, it has turned out that rigidity can be enhanced while an increase in weight and volume of the casing 7 being curbed. In particular, it has turned out that the ribs 724 each connecting holding recess portions 721 each disposed at a substantially center of a relevant one of the edges of the outer shape of the rear cover 72 are highly effective. Further, it has turned out that ribs 723 and ribs 725 each extending in a direction from a relevant edge of the edges of the frame portion of the rear cover 72 to an edge adjacent to the relevant edge, the direction being parallel to a direction of a diagonal of the rear cover 72, as viewed from the front cover 71 side including the incident surface 71a are also highly effective. However, the orientations of the ribs 723 to 725 are not limited to those illustrated in FIG. 3B and, for example, ribs may be disposed in parallel with the x-axis or the y-axis or ribs may be disposed along an outer shape of a component disposed inside. Furthermore, in the present embodiment, each of the ribs 723 to 725 may be formed in a direction in which the rib forms 45° with an edge of the outer shape of the casing 7 (rear cover 72) as viewed from the front cover 71 side including the incident surface 71a. In the case of this formation, enhancement in flexural rigidity in the directions in which the ribs form 45° with the respective edges can be expected. Providing the ribs 723 to 725 at the rear cover 72 enhances the flexural rigidity of the imaging apparatus 100 and curbs torsion of the bottom surface 72a of the rear cover 72, enabling curbing deformation and distortion of the imaging apparatus 100.

Although the present embodiment has been described in terms of the example in which the holding recess portions 721 and the battery receiving recess portion 722 are employed as recess portions to which the ribs 723 to 725 are connected, the present invention is not limited to this example. In addition, in the present embodiment, at least one of the plurality of holding recess portions 721 and the battery receiving recess portion 722 may include an opening. For example, an opening being included in the battery receiving recess portion 722 enables even a large-thickness battery to be received in the battery receiving recess portion 722.

In the present embodiment, it is desirable that as viewed from the front cover 71 side including the incident surface 71a, a maximum projected area of the recess portions provided in the rear cover 72 (for example, a maximum projected area of one of the recess portions) be no more than half a maximum area of the casing 7. This is because, as a projected area of a recess portion is larger, rigidity of the part of the area is more easily lowered, and thus, torsion is more likely to occur in the entire imaging apparatus 100. Therefore, if such configuration in which a projected area of a recess portion is large is provided, it is necessary to take a measure, such as separately disposing ribs such as those described above at the part of the projected area of the recess portion or increasing a thickness of the recess portion.

Maximum widths b' of the holding recess portions 721 illustrated in FIG. 2 are larger than a width b of the frame portion including the side surfaces 72b of the casing 7 (rear cover 72). An increase in width b of the frame portion of the rear cover 72 enhances the flexural rigidity of the rear cover 72. However, as illustrated in FIG. 2, a distance m from an effective pixel region in which a radiation image can actually be acquired in the detecting panel 1 to an outermost shape of the imaging apparatus 100 becomes larger, and therefore, the user's ease of handling can more easily be enhanced as the width b of the frame portion of the rear cover 72 is smaller. Therefore, making the maximum widths b' of the holding recess portions 721 larger than the width b of the frame portion of the rear cover 72 enables enhancement in flexural rigidity of the imaging apparatus 100 while the ease of handling the imaging apparatus 100 being enhanced.

The present embodiment has been described in terms of the form in which the components, such as the ribs 723 to 725 included in the rear cover 72, the frame portion including the side surfaces 72b, the recess portions (including the holding recess portions 721 and the battery receiving recess portion 722) and the bottom surface 72a, are integrated. However, the present invention is not limited to this form. For example, the present invention is applicable to a form including a structure in which the above-described components are separate components, some of the components being connected, some others of the components being fitted together, or a form provided using an integral molding technique that molds different kinds of materials into a single component.

As described above, in the imaging apparatus 100 according to the first embodiment, the rectangular casing 7 that contains the detecting panel 1, the detecting panel 1 detecting incident radiation R, includes the front cover 71 including the incident surface 71a on which the radiation R is incident, and the rear cover 72 disposed in such a manner as to be opposite to the front cover 71. The rear cover 72 includes one or more recess portions (the holding recess portions 721 and the battery receiving recess portion 722) and the ribs 723 and 724 (recess portion-connected ribs), at least one end of each of the ribs 723 and 724 being connected to the relevant one of the recess portions, at the bottom surface 72a opposite to the incident surface 71a. Furthermore, the rear cover 72 includes the ribs 725 (frame portion-frame portion connecting ribs) each connected to mutually adjacent edges of the frame portion including the side surfaces 72b of the casing 7 as viewed from the incident surface 71a side. Such configuration enables enhancement in rigidity of the casing 7 while limited space inside the casing of the imaging apparatus 100 being effectively used.

Second Embodiment

In the below description of the second embodiment, description of matters that are in common with those of the above-described first embodiment is omitted and matters that are different from those of the first embodiment will be described.

In an imaging apparatus 100 according to the present embodiment, also, as in the imaging apparatus 100 according to the first embodiment, a casing 7 includes two components of a front cover 71 including an incident surface 71a and a rear cover 72 including a bottom surface 72a and side surfaces 72b. Additionally, in the imaging apparatus 100 according to the second embodiment, as in the imaging apparatus 100 according to the first embodiment illustrated in FIG. 2, e.g., a detecting panel 1, a buffering member 3, a flexible circuit board 4, a control board 5 and a support base 6 are provided inside the casing 7.

Figure 4A:
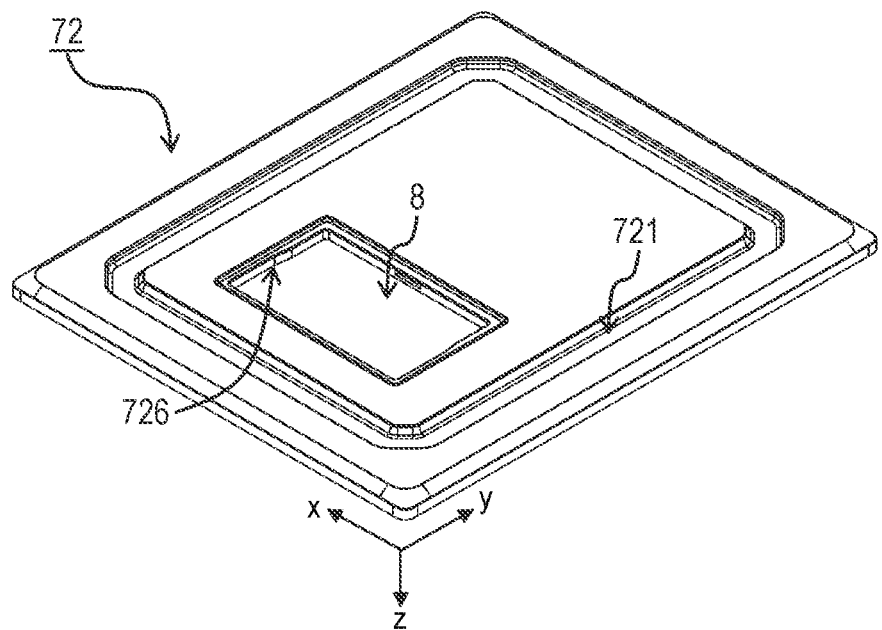
FIG. 4A is a perspective diagram illustrating an example of a schematic configuration of a rear cover in an imaging apparatus according to a second embodiment.
Figure 4B:
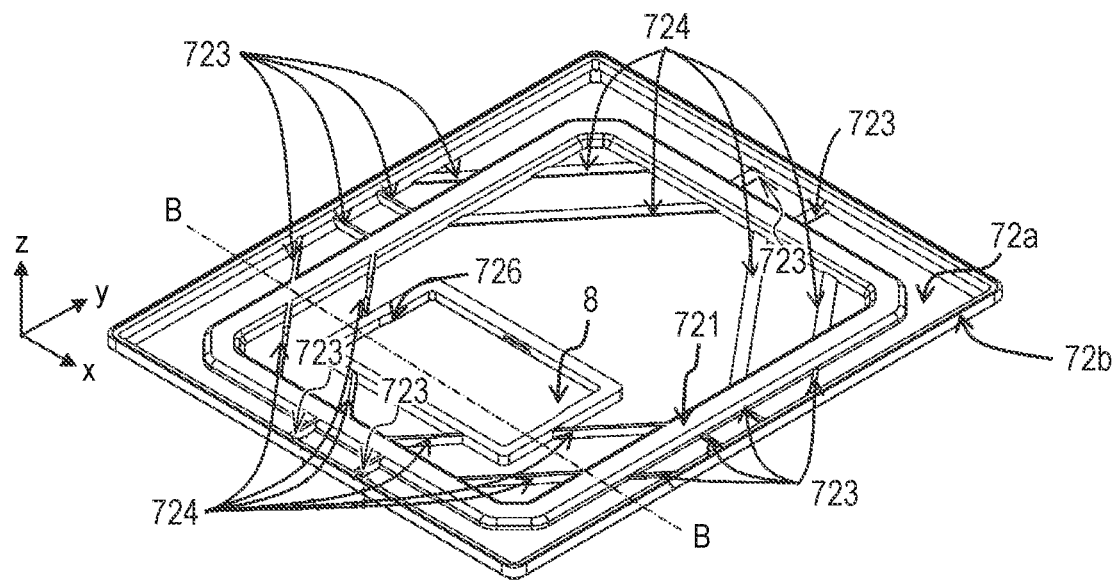
FIG. 4B is a perspective diagram illustrating an example of a schematic configuration of the rear cover in the imaging apparatus according to the second embodiment.

FIG. 4A and FIG. 4B are diagrams each illustrating an example of a schematic configuration of the rear cover 72 in the imaging apparatus 100 according to the present embodiment. In FIG. 4A and FIG. 4B, components that are similar to those illustrated in FIG. 1A to FIG. 3B are provided with reference numerals that are the same as those in FIG. 1A to FIG. 3B, and detailed description thereof is omitted. Further, in FIG. 4A and FIG. 4B, an x-y-z coordinate system corresponding to the x-y-z coordinate system illustrated in FIG. 1A to FIG. 3B is indicated.

More specifically, FIG. 4A is a perspective diagram illustrating an example of an outer appearance of the rear cover 72 as viewed in a direction that is the same as that of FIG. 3A. FIG. 4B is a perspective diagram illustrating an example of an outer appearance of the rear cover 72 as viewed from the side opposite to that of FIG. 4A (front cover 71 side of the casing 7).

In the imaging apparatus 100 according to the present embodiment, as illustrated in FIG. 4A and FIG. 4B, a holding recess portion 721 is formed in the rear cover 72 in such a manner as to be looped along an outer periphery of the casing 7 as viewed from the incident surface 71a side (z-direction side) of the casing 7. Forming a holding recess portion 721 in the rear cover 72 in such a manner as to be looped along the outer periphery of the casing 7 increases an area that a user can hold and also contributes to enhancement in flexural rigidity of the rear cover 72.

FIG. 5 is a diagram illustrating an example of an internal configuration of the rear cover 72 according to the present embodiment in a section along B-B indicated in FIG. 4B. In FIG. 5, components that are similar to those illustrated in FIG. 4A and FIG. 4B are provided with reference numerals that are the same as those in FIG. 4A and FIG. 4B, and detailed description thereof is omitted. Further, in FIG. 5, an x-y-z coordinate system corresponding to the x-y-z coordinate system illustrated in FIG. 4A and FIG. 4B is indicated.

As illustrated in FIG. 4A to FIG. 5, an opening for mounting a battery (not illustrated) is provided in the bottom surface 72a of the rear cover 72, and a battery cover attaching recess portion 726 to which a battery cover 8 is attached is provided around the opening. Here, the battery cover 8 is attached to the rear cover 72 and can be attached and detached by the user, and the battery can also be mounted and removed by the user. Further, in order to provide a waterproof structure, waterproof packing (not illustrated) may be provided at a surface of joining between the battery cover 8 and the rear cover 72. In this case, the waterproof packing is disposed at a position at which the waterproof packing is held between the battery cover 8 and the rear cover 72. Here, the battery cover 8 receives a reactive force from the waterproof packing, and thus, needs rigidity enough to endure the reactive force. Therefore, for enhancement in rigidity of the battery cover 8, standing walls are provided at the periphery of the battery cover 8. Here, a height from a surface in which the battery cover 8 is seen in the outer appearance to an end of a standing wall is 3.0 mm. In addition, when the battery cover 8 is attached, the standing wall portion is disposed in the battery cover attaching recess portion 726 of the rear cover 72. Therefore, the battery cover attaching recess portion 726 needs to have a depth according to the standing wall height. Here, the battery cover 8 can include a material such as an aluminum alloy, a magnesium alloy, a fiber reinforced resin or a resin in consideration of weight reduction; however, in the present embodiment, the material is not limited to these examples.

In the imaging apparatus 100 according to the present embodiment, as described above, the holding recess portion 721 is provided in the rear cover 72 in such a manner as to be looped along the outer periphery of the casing 7 as viewed from the incident surface 71a side of the casing 7 (z-direction side) and contributes to enhancement in flexural rigidity of the rear cover 72. However, a major part of the bottom surface 72a of the rear cover 72 has a planar shape and thus may be distorted upon deformation of the imaging apparatus 100 due to, e.g., an environment of use or an external force. Therefore, in the second embodiment, also, as in the first embodiment, rigidity of the rear cover 72 is enhanced by forming ribs 723 and ribs 724 at the bottom surface 72a of the rear cover 72. Here, in the present embodiment, each of the ribs 723 and the ribs 724 corresponds to a "recess portion-connected rib", at least one end of which is connected to the holding recess portion 721 or the battery cover attaching recess portion 726. More specifically, each of the ribs 723 is a rib connected to a frame portion including the side surfaces 72b of the casing 7 and to the holding recess portion 721. Each of the ribs 724 is a rib connected to recess portions (to parts of the holding recess portion 721 or to the holding recess portion 721 and to the battery cover attaching recess portion 726).

Although not illustrated in FIG. 4A, as in the ribs 725 in FIG. 3B, ribs each connected to edges (more specifically, mutually adjacent edges) of the frame portion including the side surfaces 72b of the rear cover 72 may be provided. In addition, even where it is difficult to connect the respective recess portions (including the holding recess portion 721 and the battery cover attaching recess portion 726) and/or parts of the frame portion via ribs or where it is difficult to connect inner portions of the holding recess portion 721 via ribs, even merely connecting the recess portions (including the holding recess portion 721 and the battery cover attaching recess portion 726), which have high rigidity, and ribs is effective for enhancement in flexural rigidity of the entire rear cover 72 relative to the weight of the casing 7.

The frame portion including the side surfaces 72b of the rear cover 72, and the holding recess portion 721 contribute to enhancement in flexural rigidity in, e.g., an x-direction and a y-direction but is less likely to contribute to flexural rigidity in directions of diagonals in an x-y plane of the rear cover 72 because of the shapes thereof. Therefore, the present inventor studied directions in which the ribs 723 and 724 are oriented in consideration of maximization of flexural rigidity (minimization of mechanical compliance) in the directions of the diagonals of the rear cover 72 relative to the weight of the casing 7.

More specifically, as in the first embodiment, with regard to orientations of the ribs 723 and 724, the present inventor conceived of forming the ribs 723 and 724 in directions that are substantially parallel to the directions of the diagonals of the rear cover 72 of the casing 7 in the x-y plane as viewed from the front cover 71 side including the incident surface 71a. Further, in the present embodiment, each of the ribs 723 and 724 may be formed in a direction in which the rib forms 45° with an edge of an outer shape of the casing 7 (rear cover 72) as viewed from the front cover 71 side including the incident surface 71a. In the case of this formation, enhancement in flexural rigidity in the directions in which the ribs form 45° with the respective edges can be expected. Furthermore, as in the first embodiment, depending on the disposition of internal components inside the casing 7, heights of the ribs 723 to 724 may be changed and in consideration of, e.g., wirings, each of relevant ribs may include a cut or the like in a part thereof, as appropriate.

The present embodiment has been described in terms of the form in which the components, such as the ribs 723 to 724 included in the rear cover 72, the frame portion including the side surfaces 72b, the recess portions (including the holding recess portion 721 and the battery cover attaching recess portion 726) and the bottom surface 72a, are integrated. However, the present invention is not limited to this form. For example, the present invention is applicable to a form including a structure in which the above-described components are separate components, some of the components being connected, some others of the components being fitted together, or a form provided using an integral molding technique that molds different kinds of materials into a single component.

As described above, in the imaging apparatus 100 according to the present embodiment, for example, various types of recess portions (including the holding recess portion 721 and the battery cover attaching recess portion 726) and the frame portion, which have functions of, e.g., being held or waterproofing and contribute to rigidity enhancement, are connected via the ribs 723, the inner parts of the holding recess portion 721 formed in such a manner as to be looped along the outer periphery of the casing 7 are connected via the ribs 724 and high-rigidity recess portions and ribs are connected. Such configuration enables enhancing rigidity of the casing 7 while effectively using limited space inside the casing of the imaging apparatus 100.

Third Embodiment

In the below description of the third embodiment, description of matters that are in common with those of the above-described first and second embodiments is omitted and matters that are different from those of the first and second embodiments will be described.

In the imaging apparatus 100 according to the present embodiment, also, as in the imaging apparatuses 100 according to the first and second embodiments, a casing 7 includes two components of a front cover 71 including an incident surface 71a and a rear cover 72 including a bottom surface 72a and side surfaces 72b.

Figure 6A:
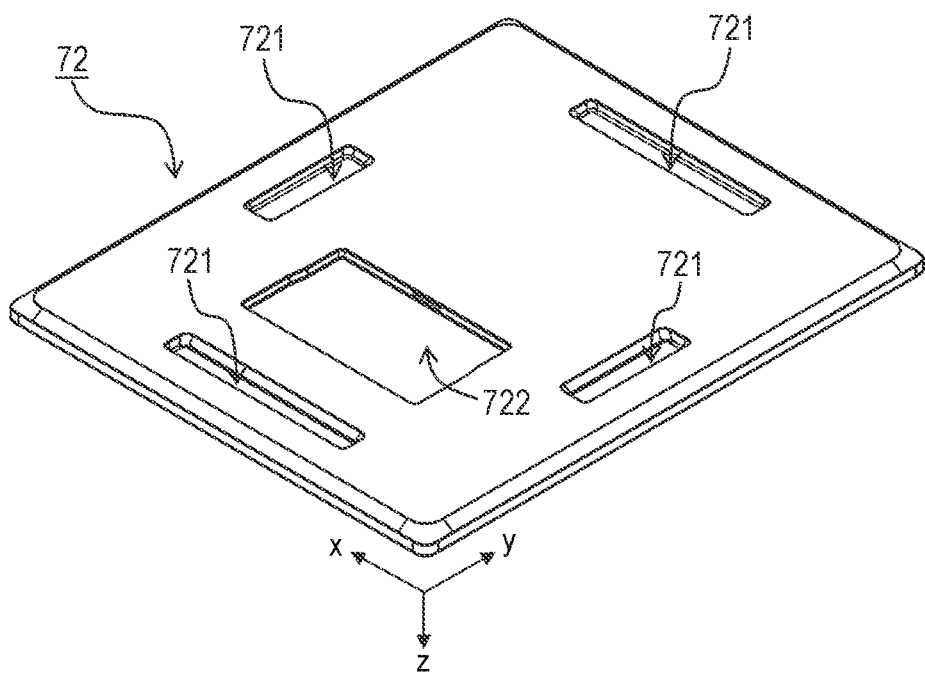
FIG. 6A is a perspective diagram illustrating an example of a schematic configuration of a rear cover in an imaging apparatus according to a third embodiment.
Figure 6B:
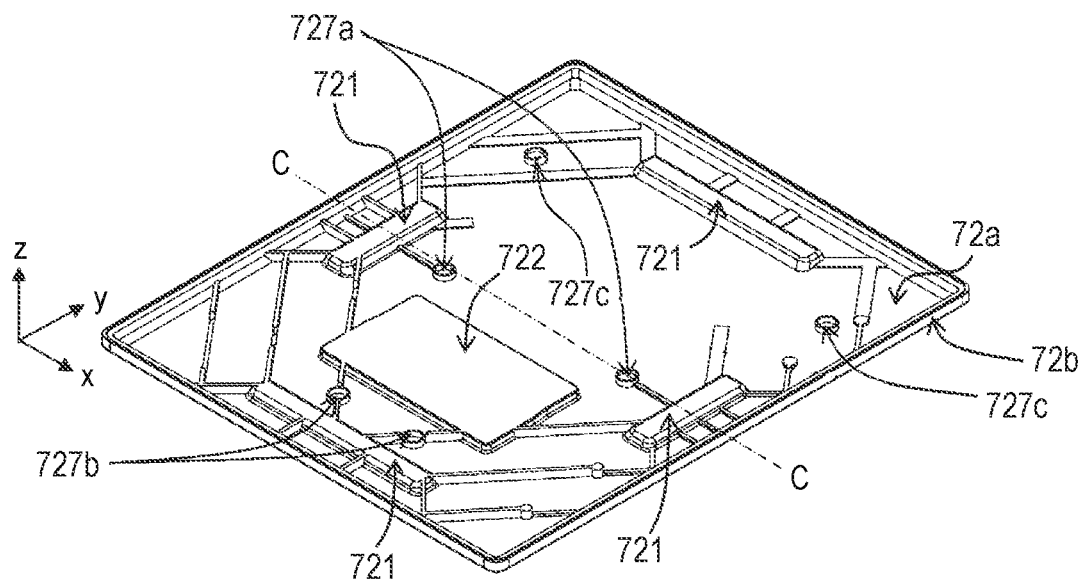
FIG. 6B is a perspective diagram illustrating an example of a schematic configuration of the rear cover in the imaging apparatus according to the third embodiment.

FIG. 6A and FIG. 6B are diagrams each illustrating an example of a schematic configuration of the rear cover 72 in the imaging apparatus 100 according to the present embodiment. In FIG. 6A and FIG. 6B, components that are similar to those illustrated in FIG. 1A to FIG. 5 are provided with reference numerals that are the same as those in FIG. 1A to FIG. 5, and detailed description thereof is omitted. Further, in FIG. 6A and FIG. 6B, an x-y-z coordinate system corresponding to the x-y-z coordinate system indicated in FIG. 1A to FIG. 5 is indicated.

More specifically, FIG. 6A is a perspective diagram illustrating an example of an outer appearance of the rear cover 72 as viewed in a direction that is the same as that of FIG. 3A. FIG. 6B is a perspective diagram illustrating an example of an outer appearance of the rear cover 72 as viewed from the side opposite to that of FIG. 6A (front cover 71 side of the casing 7).

Figure 7:
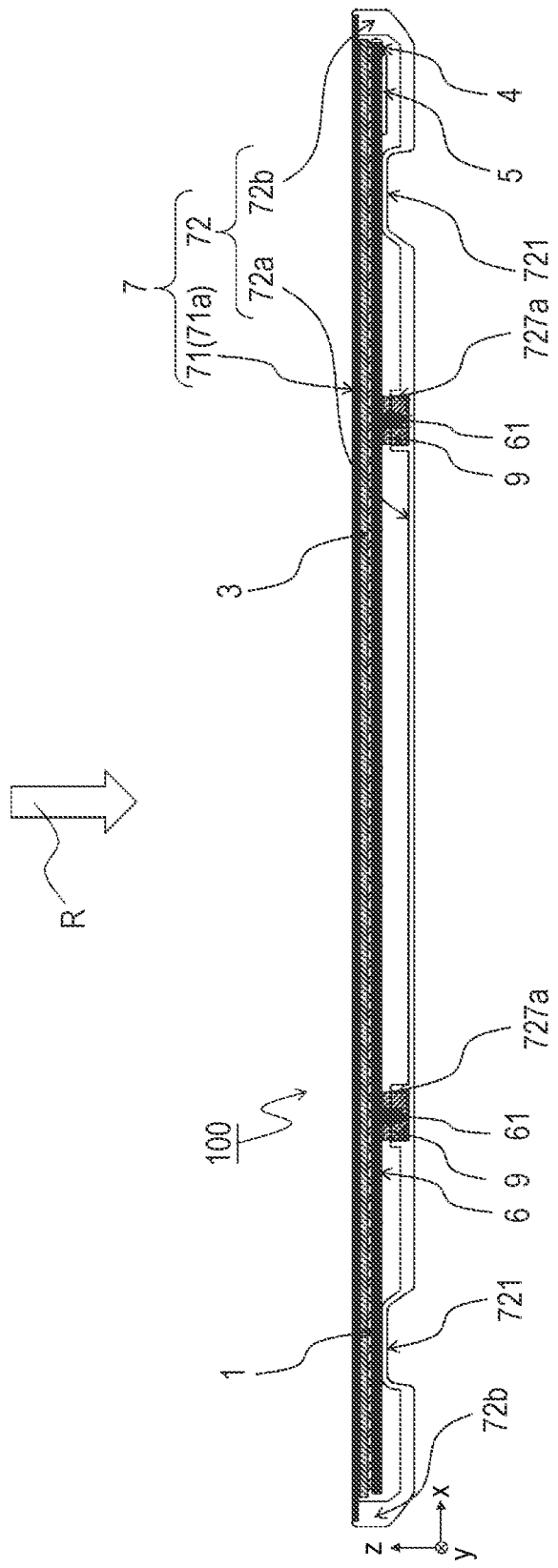
FIG. 7 is a sectional diagram illustrating an example of an internal configuration in a section along C-C indicated in FIG. 6B.

FIG. 7 is a diagram illustrating an example of an internal configuration of the imaging apparatus 100 according to the present embodiment in a section along C-C indicated in FIG. 6B. In FIG. 7, components that are similar to those illustrated in FIG. 1A to FIG. 6B are provided with reference numerals that are the same as those in FIG. 1A to FIG. 6B, and detailed description thereof is omitted. Further, in FIG. 7, an x-y-z coordinate system corresponding to the x-y-z coordinate system indicated in FIG. 1A to FIG. 6B is indicated.

As illustrated in FIG. 7, as in the imaging apparatus 100 according to the first embodiment illustrated in FIG. 2, the imaging apparatus 100 according to the present embodiment also includes a detecting panel 1, a buffering member 3, a flexible circuit board 4, a control board 5 and a support base 6 inside the casing 7.

As illustrated in FIG. 6A and FIG. 6B, in the rear cover 72 in the third embodiment, as in the first embodiment, holding recess portions 721 and a battery receiving recess portion 722 are formed. More specifically, as illustrated in FIG. 6A and FIG. 6B, the holding recess portions 721 are provided near respective edges of an outer shape of the rear cover 72, respectively, as viewed from the front cover 71 side (z-direction) including the incident surface 71a on which radiation R is incident.

Furthermore, in the rear cover 72 in the present embodiment, as in the first embodiment, in order to curb an increase in weight of the casing 7 and an increase in volume inside the casing 7 while enhancing rigidity of imaging apparatus 100, as illustrated in FIG. 6B, ribs corresponding to the ribs 723 to 725 in FIG. 3B are formed.

In the present embodiment, also, as in the second embodiment, if a holding recess portion 721 is provided in the rear cover 72 in such a manner as to be looped along an outer periphery of the casing 7, ribs each connecting inner portions of the holding recess portion 721 may be formed.

Further, even where it is difficult to connect the respective recess portions (including the holding recess portions 721 and the battery receiving recess portion 722) and/or parts of a frame portion via ribs or connecting the inner portions of the recess portion via ribs, even merely connecting the recess portions (including the holding recess portions 721 and the battery receiving recess portion 722), which have high rigidity, and ribs is effective for enhancement in flexural rigidity of the entire rear cover 72 relative to the weight of the casing 7.

Note that in the present embodiment, some of the ribs are adjusted in height in order to prevent interference with, e.g., an electric board (not illustrated) or a cable (not illustrated) disposed inside the casing 7. Furthermore, there are also ribs each including a cut in a part thereof to allow easy disposition of the cable, etc.

In the present embodiment illustrated in FIG. 6B, also, as in the first embodiment, with regard to orientations of the ribs corresponding to the ribs 723 to 725 in FIG. 3B, the ribs are formed in directions that are substantially parallel to directions of diagonals of the rear cover 72 of the casing 7 in an x-y plane as viewed from the front cover 71 side including the incident surface 71a. In the present embodiment, each of the ribs corresponding to the ribs 723 to 725 in FIG. 3B may be formed in a direction in which the rib forms 45° with an edge of the outer shape of the casing 7 (rear cover 72) as viewed from the front cover 71 side including the incident surface 71a. In the case of this formation, enhancement in flexural rigidity in the directions in which the ribs form 45° with the respective edges can be expected.

Moreover, in the rear cover 72 in the present embodiment, as illustrated in FIG. 6B, cylindrical bosses 727a to 727c, which are insertion portions for bosses 61 of the support base 6, which are illustrated in FIG. 7, are provided. Each of the bosses 727a is a cylindrical boss provided at another end of a rib connected to a holding recess portion 721. Further, each of the bosses 727b is a cylindrical boss provided at an intermediate position in a rib connected to a holding recess portion 721 and the battery receiving recess portion 722. Furthermore, each of the bosses 727c is a cylindrical boss provided independently from the ribs.

As illustrated in FIG. 7, in each of the cylindrical bosses 727a, a boss 61 of the support base 6 is disposed in such a manner as to be opposite a center of the cylindrical boss 727a when the imaging apparatus 100 is assembled. In addition, for electric insulation between the bosses 727a of the rear cover 72 and the bosses 61 of the support base 6, insulators 9 are disposed between the bosses 727a of the rear cover 72 and the bosses 61 of the support base 6, respectively. Consequently, when an external force is applied to the casing 7, the support base 6 comes into contact with the rear cover 72 via the insulators 9 along with deformation of the rear cover 72, enabling enhancement in rigidity of the entire imaging apparatus 100. Note that the disposition relationship between the support base 6 and the rear cover 72 is not limited to the form illustrated in FIG. 7, and the support base 6 may be fastened via screws from the outer appearance side of the rear cover 72. In addition, the overall rigidity may be enhanced by joining respective wide surfaces of the support base 6 and the rear cover 72 using, e.g., a gluing agent or an adhesive agent.

The present embodiment has been described in terms of the form in which the components, such as the ribs corresponding to the ribs 723 to 725 in FIG. 3B, the ribs being included in the rear cover 72, the frame portion including the side surfaces 72b, the recess portions (including the holding recess portions 721 and the battery receiving recess portions 722) and the bottom surface 72a, are integrated. However, the present invention is not limited to this form. For example, the present invention is applicable to a form including a structure in which the above-described components are separate components, some of the components being connected, some others of the components being fitted together, or a form provided using an integral molding technique that molds different kinds of materials into a single component.

As in the above-described first and second embodiments, the imaging apparatus 100 according to the present embodiment also enables enhancing the rigidity of the casing 7 while efficiently using limited space inside the casing of the imaging apparatus 100.

The above-described first to third embodiments of the present invention each enable enhancing rigidity of a casing of an imaging apparatus while efficiently using limited space inside the casing.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-018275, filed Feb. 8, 2021, which is hereby incorporated by reference herein in its entirety.

What is claimed is:

1. A radiation imaging apparatus comprising:
a radiation detecting panel arranged to detect incident radiation;
a support base that supports the radiation detecting panel, the support base having a boss on the opposite side from a surface supporting the radiation detecting panel; and
a casing arranged to contain the radiation detecting panel and the support base, the casing including a front cover including an incident surface on which the radiation is incident, and a rear cover arranged opposite to the front cover,
wherein the rear cover includes a holding portion recessed toward the incident surface, an insertion portion for the boss of the support base to be inserted therein, and a holding portion-connected rib connected to an inner surface of the holding portion at one end and to the insertion portion at the other end, and
wherein, in a direction perpendicular to the incident surface, the holding portion and the holding portion-connected rib have at least half a length of the casing or have a length of at least 5 mm.

2. The radiation imaging apparatus according to claim 1, wherein the holding portion is formed in a manner to be looped along an outer periphery of the casing as viewed from the incident surface side; and
the holding portion-connected rib is connected to the inner surface of the holding portion formed in a manner to be looped.

3. The radiation imaging apparatus according to claim 1, wherein the holding portion includes a plurality of holding portions;
the rear cover includes the plurality of holding portions in the bottom surface;
the rear cover further includes another holding portiong-connected rib; and
the another holding portion-connected rib is connected to at least two holding portions of the plurality of holding portions.

4. The radiation imaging apparatus according to claim 3, wherein the at least two holding portions are provided near mutually adjacent two edges of an outer shape of the rear cover, respectively, as viewed from the incident surface side; and
the another holding portion-connected rib is connected to the at least two holding portions provided near the mutually adjacent two edges respectively.

5. The radiation imaging apparatus according to claim 1, wherein the rear cover includes a frame portion to be joined to the front cover at an outer periphery of the rear cover;
the rear cover further includes another holding portion-connected rib; and
the another holding portion-connected rib is connected to the frame portion and to the holding portion.

6. The radiation imaging apparatus according to claim 5, wherein the rear cover further includes a frame portion-to-frame portion connecting rib connected to mutually adjacent edges of the frame portion as viewed from the incident surface side.

7. The radiation imaging apparatus according to claim 1, wherein the holding portion-connected rib is formed in a direction that is substantially parallel to a direction of a diagonal of the casing as viewed from the incident surface side.

8. The radiation imaging apparatus according to claim 1, wherein the holding portion-connected rib is formed in a direction in which the recess portion-connected rib forms 45° with an outer shape of the casing as viewed from the incident surface side.

9. The radiation imaging apparatus according to claim 1, wherein the holding portion is a portion for a user to hold the casing.

10. The radiation imaging apparatus according to claim 1, further comprising a battery receiving recess portion for receiving a battery.

11. The radiation imaging apparatus according to claim 1, wherein a maximum projected area of the holding portion is no more than half an area of the casing as viewed from the incident surface side.

12. The radiation imaging apparatus according to claim 1, wherein holding portion includes a plurality of holding portions;
the rear cover includes the plurality of holding portions in the bottom surface; and
at least one of the plurality of holding portions includes an opening.

13. The radiation imaging apparatus according to claim 1, wherein a position of a maximum height portion of the holding portion-connected rib and a position of an inner surface of the casing at a maximum depth portion of the holding portion coincide with each other in a thickness direction of the casing.

* * * * *